(12) United States Patent
Yokhin et al.

(10) Patent No.: US 8,243,878 B2
(45) Date of Patent: Aug. 14, 2012

(54) HIGH-RESOLUTION X-RAY DIFFRACTION MEASUREMENT WITH ENHANCED SENSITIVITY

(75) Inventors: Boris Yokhin, Nazareth Illit (IL); Isaac Mazor, Haifa (IL); Alexander Krohmal, Haifa (IL); Amos Gvirtzman, Moshav Zippori (IL); Gennady Openganden, Kiryat Yam (IL); David Berman, Tivon (IL); Matthew Wormington, Littleton, CO (US)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 322 days.

(21) Appl. No.: 12/683,436

(22) Filed: Jan. 7, 2010

(65) Prior Publication Data

US 2011/0164730 A1     Jul. 7, 2011

(51) Int. Cl.
*G01N 23/20* (2006.01)
*G01N 23/203* (2006.01)
*G01N 23/207* (2006.01)

(52) U.S. Cl. .......... 378/71; 378/70; 378/72; 378/76

(58) Field of Classification Search ............ 378/70–90
See application file for complete search history.

(56) References Cited

U.S. PATENT DOCUMENTS

| | | |
|---|---|---|
| 2,805,342 A | 9/1957 | Lang |
| 4,242,588 A | 12/1980 | Silk et al. |
| 4,446,568 A | 5/1984 | Williams et al. |
| 4,696,024 A | 9/1987 | Pesch |
| 4,725,963 A | 2/1988 | Taylor et al. |
| 4,847,882 A | 7/1989 | Knoth et al. |
| 4,989,226 A | 1/1991 | Woodbury et al. |
| 5,151,588 A | 9/1992 | Kiri et al. |
| 5,340,988 A | 8/1994 | Kingsley et al. |
| 5,373,544 A | 12/1994 | Goebel |
| 5,481,109 A | 1/1996 | Ninomiya et al. |
| 5,530,732 A * | 6/1996 | Takemi ................. 378/73 |
| 5,574,284 A | 11/1996 | Farr |
| 5,619,548 A | 4/1997 | Koppel |
| 5,740,226 A | 4/1998 | Komiya et al. |
| 5,850,425 A | 12/1998 | Wilkins |
| 5,900,645 A | 5/1999 | Yamada |
| 5,923,720 A | 7/1999 | Barton et al. |

(Continued)

FOREIGN PATENT DOCUMENTS

JP    3075548 A    3/1991

(Continued)

OTHER PUBLICATIONS

Paul F. Fewster, "X-ray analysis of thin films and multilayers," Rep. Prog. Phys. 59, (1996), 1339-1407.*

(Continued)

*Primary Examiner* — Allen C. Ho
(74) *Attorney, Agent, or Firm* — D. Kligler I.P. Services Ltd.

(57) ABSTRACT

A method for analysis includes directing a converging beam of X-rays toward a surface of a sample having an epitaxial layer formed thereon, and sensing the X-rays that are diffracted from the sample while resolving the sensed X-rays as a function of angle so as to generate a diffraction spectrum including a diffraction peak and fringes due to the epitaxial layer. A characteristic of the fringes is analyzed in order to measure a relaxation of the epitaxial layer.

42 Claims, 9 Drawing Sheets

U.S. PATENT DOCUMENTS

| | | | |
|---|---|---|---|
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,317,483 B1 | 11/2001 | Chen | |
| 6,331,890 B1 | 12/2001 | Marumo et al. | |
| 6,381,303 B1 | 4/2002 | Vu et al. | |
| 6,389,102 B2 | 5/2002 | Mazor et al. | |
| 6,453,006 B1 | 9/2002 | Koppel et al. | |
| 6,459,763 B1* | 10/2002 | Koinuma et al. | 378/71 |
| 6,504,902 B2 | 1/2003 | Iwasaki et al. | |
| 6,507,634 B1 | 1/2003 | Koppel et al. | |
| 6,512,814 B2 | 1/2003 | Yokhin et al. | |
| 6,556,652 B1 | 4/2003 | Mazor et al. | |
| 6,574,305 B2 | 6/2003 | Boer et al. | |
| 6,625,250 B2 | 9/2003 | Houge | |
| 6,639,968 B2 | 10/2003 | Yokhin et al. | |
| 6,643,354 B2 | 11/2003 | Koppel et al. | |
| 6,665,372 B2 | 12/2003 | Bahr et al. | |
| 6,680,996 B2 | 1/2004 | Yokhin et al. | |
| 6,711,232 B1 | 3/2004 | Janik | |
| 6,718,008 B1* | 4/2004 | He et al. | 378/71 |
| 6,744,850 B2 | 6/2004 | Fanton et al. | |
| 6,744,950 B2 | 6/2004 | Aleksoff | |
| 6,750,952 B2 | 6/2004 | Grodnensky et al. | |
| 6,754,304 B1 | 6/2004 | Kumakhov | |
| 6,754,305 B1 | 6/2004 | Rosencwaig et al. | |
| 6,768,785 B2 | 7/2004 | Koppel et al. | |
| 6,771,735 B2 | 8/2004 | Janik et al. | |
| 6,807,251 B2* | 10/2004 | Okanda et al. | 378/71 |
| 6,810,105 B2 | 10/2004 | Nasser-Ghodsi et al. | |
| 6,813,338 B2 | 11/2004 | Takata et al. | |
| 6,879,051 B1 | 4/2005 | Singh et al. | |
| 6,895,075 B2 | 5/2005 | Yokhin et al. | |
| 6,898,270 B2 | 5/2005 | Lange et al. | |
| 6,937,694 B2* | 8/2005 | Yokoyama et al. | 378/78 |
| 6,947,520 B2 | 9/2005 | Yokhin et al. | |
| 6,963,630 B2 | 11/2005 | Umezawa et al. | |
| 6,970,532 B2 | 11/2005 | Hayashi et al. | |
| 6,987,832 B2 | 1/2006 | Koppel et al. | |
| 6,996,208 B2 | 2/2006 | Helming et al. | |
| 6,999,557 B2* | 2/2006 | Yamaguchi et al. | 378/71 |
| 7,003,075 B2 | 2/2006 | Miyake et al. | |
| 7,035,373 B2* | 4/2006 | Omote | 378/79 |
| 7,062,013 B2 | 6/2006 | Berman et al. | |
| 7,068,753 B2 | 6/2006 | Berman et al. | |
| 7,076,024 B2 | 7/2006 | Yokhin | |
| 7,110,491 B2 | 9/2006 | Mazor et al. | |
| 7,113,566 B1* | 9/2006 | Peled et al. | 378/70 |
| 7,116,754 B2* | 10/2006 | Lischka et al. | 378/79 |
| 7,120,227 B2* | 10/2006 | Ozawa et al. | 378/87 |
| 7,120,228 B2 | 10/2006 | Yokhin et al. | |
| 7,158,608 B2 | 1/2007 | Kucharczyk | |
| 7,213,686 B2 | 5/2007 | Kaufman | |
| 7,231,016 B2 | 6/2007 | Berman et al. | |
| 7,242,743 B2 | 7/2007 | Fewster | |
| 7,242,745 B2 | 7/2007 | He et al. | |
| 7,258,485 B2 | 8/2007 | Nakano et al. | |
| 7,406,153 B2* | 7/2008 | Berman | 378/86 |
| 7,474,732 B2 | 1/2009 | Berman et al. | |
| 7,483,513 B2 | 1/2009 | Mazor et al. | |
| 7,551,719 B2 | 6/2009 | Yokhin et al. | |
| 7,742,564 B2* | 6/2010 | Parham et al. | 378/71 |
| 2003/0123610 A1 | 7/2003 | Okanda et al. | |
| 2003/0157559 A1 | 8/2003 | Omote et al. | |

FOREIGN PATENT DOCUMENTS

| | | |
|---|---|---|
| JP | 5188019 A | 7/1993 |
| JP | 666741 A | 3/1994 |
| JP | 6258260 A | 9/1994 |
| JP | 6273357 A | 9/1994 |
| JP | 7311163 A | 11/1995 |
| JP | 8-313458 A | 11/1996 |
| JP | 9210663 A | 8/1997 |
| JP | 9-229879 A | 9/1997 |
| JP | 10048398 A | 2/1998 |
| JP | 10160688 A | 6/1998 |
| JP | 10206354 A | 8/1998 |
| JP | 10318949 A | 12/1998 |
| JP | 11-14562 A | 1/1999 |
| JP | 11014561 A | 1/1999 |
| JP | 11304728 | 11/1999 |
| JP | 11304728 A | 11/1999 |
| JP | 200088776 A | 3/2000 |
| JP | 2000266698 A | 9/2000 |
| JP | 2000292379 A | 10/2000 |
| JP | 2000314708 A | 11/2000 |
| JP | 200166398 A | 3/2001 |
| JP | 2001153822 A | 6/2001 |
| JP | 2003194741 A | 7/2003 |
| JP | 2003329619 A | 11/2003 |
| JP | 2004257914 A | 9/2004 |
| JP | 2005172830 A | 6/2005 |
| JP | 2005214712 A | 8/2005 |
| JP | 2005265841 A | 9/2005 |
| JP | 2005315742 A | 11/2005 |
| JP | 2005326261 A | 11/2005 |
| JP | 2006317249 A | 11/2006 |
| WO | 2004013867 A2 | 2/2004 |

OTHER PUBLICATIONS

Japanese Patent Application # 2006114489 Official Action dated Jun. 14, 2011.

Japanese Patent Application # 2006194756 Official Action dated Jul. 26, 2011.

U.S. Appl. No. 12/958,420, filed Dec. 2, 2010.

U.S. Appl. No. 13/180,568, filed Jul. 12, 2011.

Japanese Patent Application # 2005273641 Official Action dated Oct. 28, 2010.

Japanese Patent Application # 2005274293 Official Action dated Dec. 21, 2010.

Pesek et al., "Lattice Misfit and Relative Tilt of Lattice Planes in Semiconductor Heterostructures", Semiconductor Science and Technology Journal, vol. 6, pp. 705-708, IOP Publishing Ltd 1991.

Japanese Patent Application # 2006114489 Official Action dated Nov. 30, 2010.

He, B., "Two-dimensional X-ray Diffraction", pp. 356-359, Published by John Wiley & Sons, Inc., USA, 2009.

Bowen et al., "X-Ray metrology by Diffraction and Reflectivity," CP550, Characterization and Metrology for ULSI Technology: 2000 International Conference, pp. 570-579, American Institute of Physics, 2001.

Cohen et al., "Characterization of the silicon on insulator film in bonded wafers by high resolution x-ray diffraction", Applied Physics Letters, vol. 75, No. 6, pp. 787-789, Aug. 9, 1999.

Cohen et al., "High-Resolution X-Ray Diffraction for Characterization and Monitoring of Silicon-on-Insulator Fabrication Processes," Journal of Applied Physics, vol. 93, No. 1, pp. 245-250, Jan. 1, 2003.

Goorsky et al., "Grazing Incidence In-plane Diffraction Measurement of In-plane Mosaic with Microfocus X-ray Tubes", Crystal Research and Technology, vol. 37, No. 7, pp. 645-653, year 2002.

Hayashi et al., "Refracted X-Rays Propagating Near the Surface under Grazing Incidence Condition," Spectrochimica Acta, Part B 54, pp. 227-230, year 1999.

Hu et al., "Small angle x-ray scattering metrology for sidewall angle and cross section of nanometer scale line gratings," Journal of Applied Physics, vol. 96, No. 4, pp. 1983-1987, Aug. 15, 2004.

Guerault, H., "Specular reflectivity and off-specular scattering: Tools for roughness investigation", Instituut voor Kern-en Stralingsfysica, Dec. 15, 2000.

Jones et al., "3-Dimensional Lineshape Metrology Using Small Angle X-ray Scattering", AIP Conference Proceedings, vol. 683, pp. 434-438, Sep. 30, 2003.

Jones et al., "Sub-Nanometer Wavelength Metrology of Lithographically Prepared Structures: A Comparison of Neutron and X-Ray Scattering", Proceedings of SPIE—the International Society for Optical Engineering, Jun. 1, 2003.

Jones et al., "Small Angle X-ray Scattering for Ssub-100 nm Pattern Characterization," Applied Physics Letters, vol. 83, No. 19, pp. 4059-4061, Nov. 10, 2003.

Jordan Valley, "How to Measure SiGe on SOI on BedeMetrixTM Tools", Electronic Materials Conference 2008, USA, Jul. 21, 2008.

Kojima et al., "Structural Characterization of Thin Films by X-ray Reflectivity," Rigaku Journal, vol. 16, No. 2, pp. 31-41, year 1999.

Kozaczek et al., "X-ray Diffraction Metrology for 200mm Process Qualification and Stability Assessment," Advanced Metallization Conference, Canada, Oct. 8-11, 2001.

X-Ray Optical Systems, Inc., "Monolithic Polycapillary Lens Information", Albany, USA, Dec. 29, 1998.

Wu et al., "Substepping and its Application to HST Imaging", Astronomical Data Analysis Software and Systems VII ASP Conference Series, vol. 145, pp. 82-85, year 1998.

Naudon et al., "New Apparatus for Grazing X-ray Reflectometry in the Angle-Resolved Dispersive Mode," Journal of Applied Crystallography, vol. 22, pp. 460-464, year 1989.

Neissendorfer et al., "The Energy-Dispersive Reflectometer/Diffractometer at BESSY-I", Measurement Science Technology, vol. 10, pp. 354-361, IOP Publishing Ltd., year 1999.

Parrill et al., "GISAXA—Glancing Incidence Small Angle X-ray Scattering," Journal de Physique IV, vol. 3, pp. 411-417, Dec. 1993.

Powell et al., "X-ray Diffraction and Reflectivity Characterization of SiGe Superlattice", Semiconductor Science Technology Journal, vol. 7, pp. 627-631, year 1992.

Di Fonzo et al., "Non-Destructive Determination of Local Strain with 100-Nanometre Spatial Resolution," Nature, vol. 403, pp. 638-640, Feb. 10, 2000.

Ulyanenkov, A., "Introduction to High Resolution X-Ray Diffraction," Workshop on X-ray characterization of thin layers, Uckley, May 21-23, 2003.

Wall et al., U.S. Appl. No. 61/239,445 "Fast Measurement of X-ray Diffraction from Tilted Layers", filed Sep. 3, 2009.

Wiener et al., "Characterization of Titanium Nitride Layers by Grazing- Emission X-Ray Fluorescence Spectrometry", vol. 125, pp. 129-136, Elsevier Science BV 1998.

Woitok et al., "Towards Fast Reciprocal Space Mapping," JCPDS—International Centre for Diffraction Data, Advances in X-ray Analysis, vol. 48, pp. 165-169, year 2005.

Oxford Instruments Inc., Series 5000 Model XTF5011 X-Ray Tube Datasheet, Scotts Valley, USA, Jun. 28, 2000.

Japanese Patent Application # 2003549898 Official Action dated Jun. 7, 2010.

U.S. Appl. No. 09/941,723 Official Action dated Apr. 4, 2005.
U.S. Appl. No. 10/946,426 Official Action dated Feb. 6, 2006.
U.S. Appl. No. 11/018,352 Official Action dated Feb. 8, 2006.
U.S. Appl. No. 11/018,352 Official Action dated Oct. 24, 2005.
U.S. Appl. No. 11/200,857 Official Action dated Aug. 11, 2008.
U.S. Appl. No. 11/200,857 Official Action dated Aug. 27, 2007.
U.S. Appl. No. 11/200,857 Official Action dated Mar. 11, 2008.
U.S. Appl. No. 11/389,490 Official Action dated May 1, 2008.
U.S. Appl. No. 11/487,433 Official Action dated May 29, 2008.

Ryan et al., U.S. Appl. No. 61/328,645 "High-Resolution X-Ray Diffractometer" filed Apr. 28, 2010.

Authier, A., "Dynamical Theory of X-Ray Diffraction", International Union of Crystallography, Monographs on Crystallography 11, revised edition, Oxford University Press 2005.

Korean Patent Application # 10-2005-0083542 Office Action dated Feb. 15, 2012.

* cited by examiner

HIGH-RESOLUTION X-RAY DIFFRACTION MEASUREMENT WITH ENHANCED SENSITIVITY

FIELD OF THE INVENTION

The present invention relates generally to X-ray analysis, and specifically to X-ray measurement of thin film properties.

BACKGROUND OF THE INVENTION

X-ray diffractometry (XRD) is a well-known technique for studying the crystalline structure of matter. In XRD, a sample is irradiated by a monochromatic X-ray beam, and the locations and intensities of the diffraction peaks are measured. The characteristic diffraction angles and the intensity of the diffracted radiation depend on the lattice planes of the sample under study and the atoms that occupy those planes. For a given wavelength $\lambda$ and lattice plane spacing d, diffraction peaks will be observed when the X-ray beam is incident on a lattice plane at angles $\theta$ that satisfy the Bragg condition: $n\lambda=2d \sin \theta$, wherein n is the scattering order. The angle $\theta$ that satisfies the Bragg condition is known as the Bragg angle. Distortions in the lattice planes due to stress, solid solution, or other effects lead to observable changes in the XRD spectrum.

XRD has been used, inter alia, for measuring characteristics of epitaxial films produced on semiconductor wafers. For example, Bowen et al. describe a method for measuring germanium concentration in a SiGe structure using high-resolution XRD in "X-Ray metrology by Diffraction and Reflectivity," *Characterization and Metrology for ULSI Technology, 2000 International Conference* (American Institute of Physics, 2001), which is incorporated herein by reference.

XRD may also be used at grazing incidence to observe structures on the surface of a sample. For example, Goorsky et al. describe the use of grazing-incidence XRD for analyzing epitaxial layer structures on a semiconductor wafer in "Grazing Incidence In-plane Diffraction Measurement of In-plane Mosaic with Microfocus X-ray Tubes," *Crystal Research and Technology* 37:7 (2002), pages 645-653, which is incorporated herein by reference. The authors apply the technique to determine the in-plane lattice parameter and lattice orientation of very thin surface and buried semiconductor layers.

SUMMARY

Embodiments of the present invention that are described hereinbelow provide methods and systems that enhance the sensitivity and accuracy of high-resolution XRD measurements. These methods and systems are useful particularly in measuring features of epitaxial thin-film layers, but they may also be applied in analyzing crystalline structures of other types.

There is therefore provided, in accordance with an embodiment of the present invention, a method for analysis, including directing a converging beam of X-rays toward a surface of a sample having first and second crystalline layers, with different, respective crystal characteristics. The X-rays that are diffracted from the sample are sensed while resolving the sensed X-rays as a function of angle so as to generate a first diffraction spectrum including at least a first diffraction peak due to the first layer and a second diffraction peak due to the second layer. A beam blocker is positioned in the converging beam so as to block a range of angles containing the first diffraction peak, and the X-rays that are diffracted from the sample while the beam blocker is positioned in the converging beam are sensed so as to generate a second diffraction spectrum including at least the second diffraction peak while the first diffraction peak at least partly blocked. At least the second diffraction spectrum is analyzed so as to identify a characteristic of at least the second layer.

In a disclosed embodiment, sensing the X-rays includes deploying a detector array having elements configured to capture and resolve the X-rays over a range of elevation angles simultaneously, wherein the range is at least 2 degrees.

Typically, the second layer is deposited epitaxially over the first layer. In a disclosed embodiment, the first layer includes a semiconductor substrate, such as a silicon wafer, and the second layer includes a doped semiconductor, such as a SiGe epitaxial layer.

In one embodiment, analyzing at least the second diffraction spectrum includes analyzing a fringe pattern appearing in a vicinity of the first diffraction peak in the second diffraction spectrum.

Positioning the beam blocker may include automatically analyzing the first diffraction spectrum so as to identify an angular range of the first diffraction peak, and automatically shifting the blocker to cover the identified range.

In some embodiments, the converging beam of X-rays has a focus, and sensing the X-rays to generate the first diffraction spectrum includes shifting the sample out of the focus so as to increase a separation between the first and second diffraction peaks. Positioning the beam blocker includes adjusting a position of beam blocker while the sample is out of the focus, and then shifting the sample into the focus in order to generate the second diffraction spectrum. Sensing the X-rays to generate the first diffraction spectrum may include shifting the sample out of the focus and capturing at least the first diffraction spectrum in an asymmetric diffraction mode.

There is also provided, in accordance with an embodiment of the present invention, a method for analysis, including directing a converging beam of X-rays, having a focus, toward a surface of a sample having first and second crystalline layers, with different, respective crystal characteristics. The X-rays that are diffracted from the sample are sensed while resolving the sensed X-rays as a function of angle so as to generate a diffraction spectrum including at least a first diffraction peak due to the first layer and a second diffraction peak due to the second layer. The sample is shifted out of the focus so as to increase a separation between the first and second diffraction peaks in the diffraction spectrum, and the diffraction spectrum is analyzed so as to identify a characteristic of at least the second layer.

In some embodiments, the X-rays in the converging beam impinge on the sample over a range of incidence angles, and sensing the X-rays includes detecting the X-rays in an asymmetric mode, in which the X-rays are diffracted from the sample at takeoff angles that are different from the incidence angles. In one embodiment, the second layer is deposited epitaxially over the first layer, and analyzing the diffraction spectrum includes detecting a relaxation of the second layer relative to the first layer. The converging beam of the X-rays impinges on a spot on the surface of the sample, and the method, alternatively or additionally, includes positioning a beam limiter to block a portion of the X-rays in a location adjacent to the spot so as to reduce a dimension of the spot.

In a disclosed embodiment, shifting the sample includes measuring the separation as a function of a distance of the sample from the focus. Analyzing the diffraction spectrum may include finding a concentration of a dopant in the second layer based on a functional dependence of the separation on the distance of the sample from the focus.

There is additionally provided, in accordance with an embodiment of the present invention, a method for analysis, including directing a converging beam of X-rays to impinge over a range of incidence angles on a spot on a surface of a sample having an epitaxial layer formed thereon. A beam limiter is positioned to block a portion of the X-rays in a location adjacent to the spot so as to reduce a dimension of the spot. The X-rays that are diffracted from the spot are sensed in an asymmetric mode, in which the X-rays are diffracted from the sample at takeoff angles that are different from the incidence angles, while resolving the sensed X-rays as a function of angle so as to generate a diffraction spectrum. The diffraction spectrum is analyzed in order to identify a characteristic of the epitaxial layer.

In a disclosed embodiment, the beam limiter includes a knife edge, which is positioned parallel to the surface over the spot. Alternatively, the beam limiter has a hole configured for passage of the X-rays therethrough, such that the dimension of the spot is determined by a size of the hole.

Typically, either the incidence angles or the takeoff angles fall within a range of grazing angles.

There is further provided, in accordance with an embodiment of the present invention, a method for analysis, including directing a converging beam of X-rays toward a surface of a sample having an epitaxial layer formed thereon. The X-rays that are diffracted from the sample are sensed while resolving the sensed X-rays as a function of angle so as to generate a diffraction spectrum including a diffraction peak and fringes due to the epitaxial layer. A characteristic of the fringes is analyzed in order to measure a relaxation of the epitaxial layer.

In a disclosed embodiment, analyzing the characteristic includes assessing an amplitude of the fringes, wherein a reduction in the amplitude is indicative of an increase in the relaxation.

In some embodiments, the sample includes a crystalline substrate, and directing the converging beam includes positioning a beam blocker in the converging beam so as to block a range of angles containing a substrate diffraction peak while enhancing detection of the fringes at angles adjacent to the range that is blocked.

There is moreover provided, in accordance with an embodiment of the present invention, a method for analysis, including directing a converging monochromatic first beam of X-rays at a first wavelength toward a focus on a surface of a crystalline sample. A second, undesired beam at a second wavelength is blocked at a location adjacent to the first beam and before the focus. The X-rays that are diffracted from the sample are sensed while resolving the sensed X-rays as a function of angle so as to generate a diffraction spectrum of the sample. The diffraction spectrum is analyzed so as to identify a characteristic of the sample.

In a disclosed embodiment, directing the first beam includes focusing an input X-ray beam using a curved crystal monochromator, which also generates the second beam.

There is additionally provided, in accordance with an embodiment of the present invention, a method for analysis, including directing a converging beam of X-rays toward a focus on a surface of a crystalline sample. A slit is scanned across the converging beam so as to cause the X-rays in the beam to be incident on the sample at a sequence of angles of incidence over an angular range of the beam. At each of the angles of incidence, the X-rays that are diffracted from the sample are sensed while resolving the sensed X-rays as a function of takeoff angle so as to generate diffraction data with respect to each of the angles of incidence. The diffraction data with respect to the angles of incidence are combined over the angular range so as to generate a reciprocal space map of diffraction from the sample.

There is moreover provided, in accordance with an embodiment of the present invention, apparatus for analysis, including an X-ray source, which is configured to direct a converging beam of X-rays toward a surface of a sample having first and second crystalline layers, with different, respective crystal characteristics, whereby the X-rays are diffracted from the sample so as to generate a diffraction spectrum including at least a first diffraction peak due to the first layer and a second diffraction peak due to the second layer. A detector assembly is configured to sense the X-rays that are diffracted from the sample while resolving the sensed X-rays as a function of angle. A beam blocker is configured to be positioned in the converging beam so as to block a range of angles containing the first diffraction peak. A processor is coupled to receive and process an output of the detector assembly, while the range of the angles containing the first diffraction peak is blocked, so as to identify a characteristic of at least the second layer based on the diffraction spectrum.

There is furthermore provided, in accordance with an embodiment of the present invention, apparatus for analysis, including an X-ray source, which is configured to direct a converging beam of X-rays toward a surface of a sample having first and second crystalline layers, with different, respective crystal characteristics, whereby the X-rays are diffracted from the sample so as to generate a diffraction spectrum including at least a first diffraction peak due to the first layer and a second diffraction peak due to the second layer. A detector assembly is configured to sense the X-rays that are diffracted from the sample while resolving the sensed X-rays as a function of angle. A motion device is configured to shift the sample out of the focus so as to increase a separation between the first and second diffraction peaks in the diffraction spectrum. A processor is coupled to receive and process an output of the detector assembly, while the sample is shifted out of the focus, so as to identify a characteristic of at least the second layer based on the diffraction spectrum.

There is also provided, in accordance with an embodiment of the present invention, apparatus for analysis, including an X-ray source, which is configured to direct a converging beam of X-rays to impinge over a range of incidence angles on a spot on a surface of a sample having an epitaxial layer formed thereon, whereby the X-rays are diffracted from the sample so as to generate a diffraction spectrum. A beam limiter is configured to block a portion of the X-rays in a location adjacent to the spot so as to reduce a dimension of the spot. A detector assembly is configured to sense the X-rays that are diffracted from the spot in an asymmetric mode, in which the X-rays are diffracted from the sample at takeoff angles that are different from the incidence angles, while resolving the sensed X-rays as a function of angle. A processor is coupled to receive and process an output of the detector assembly so as to identify a characteristic of the epitaxial layer based on the diffraction spectrum.

There is additionally provided, in accordance with an embodiment of the present invention, apparatus for analysis, including an X-ray source, which is configured to direct a converging beam of X-rays toward a surface of a sample having an epitaxial layer formed thereon, whereby the X-rays are diffracted from the sample so as to generate a diffraction spectrum including a diffraction peak and fringes due to the epitaxial layer. A detector assembly is configured to sense the X-rays that are diffracted from the sample while resolving the sensed X-rays as a function of angle. A processor is coupled to receive and process an output of the detector assembly so as to measure a relaxation of the epitaxial layer based on a characteristic of the fringes.

There is further provided, in accordance with an embodiment of the present invention, apparatus for analysis, including an X-ray source, which is configured to direct a converging monochromatic first beam of X-rays at a first wavelength toward a focus on a surface of a crystalline sample. A beam blocker is configured to be positioned so as to block a second beam at a second wavelength at a location adjacent to the first beam and before the focus. A detector assembly is configured to sense the X-rays that are diffracted from the sample while resolving the sensed X-rays as a function of angle so as to generate a diffraction spectrum of the crystalline sample. A processor is coupled to receive and process the diffraction spectrum so as to identify a characteristic of the sample.

There is moreover provided, in accordance with an embodiment of the present invention, apparatus for analysis, including an X-ray source, which is configured to direct a converging beam of X-rays toward a focus on a surface of a crystalline sample. A slit is configured to scan across the converging beam so as to cause the X-rays in the beam to be incident on the sample at a sequence of angles of incidence over an angular range of the beam. A detector assembly is configured to sense the X-rays that are diffracted from the sample at each of the angles of incidence, while resolving the sensed X-rays as a function of takeoff angle so as to generate diffraction data with respect to each of the angles of incidence. A processor is configured to combine the diffraction data with respect to the angles of incidence over the angular range so as to generate a reciprocal space map of diffraction from the sample.

The present invention will be more fully understood from the following detailed description of the embodiments thereof, taken together with the drawings in which:

DETAILED DESCRIPTION OF EMBODIMENTS

Overview

Figure 1:
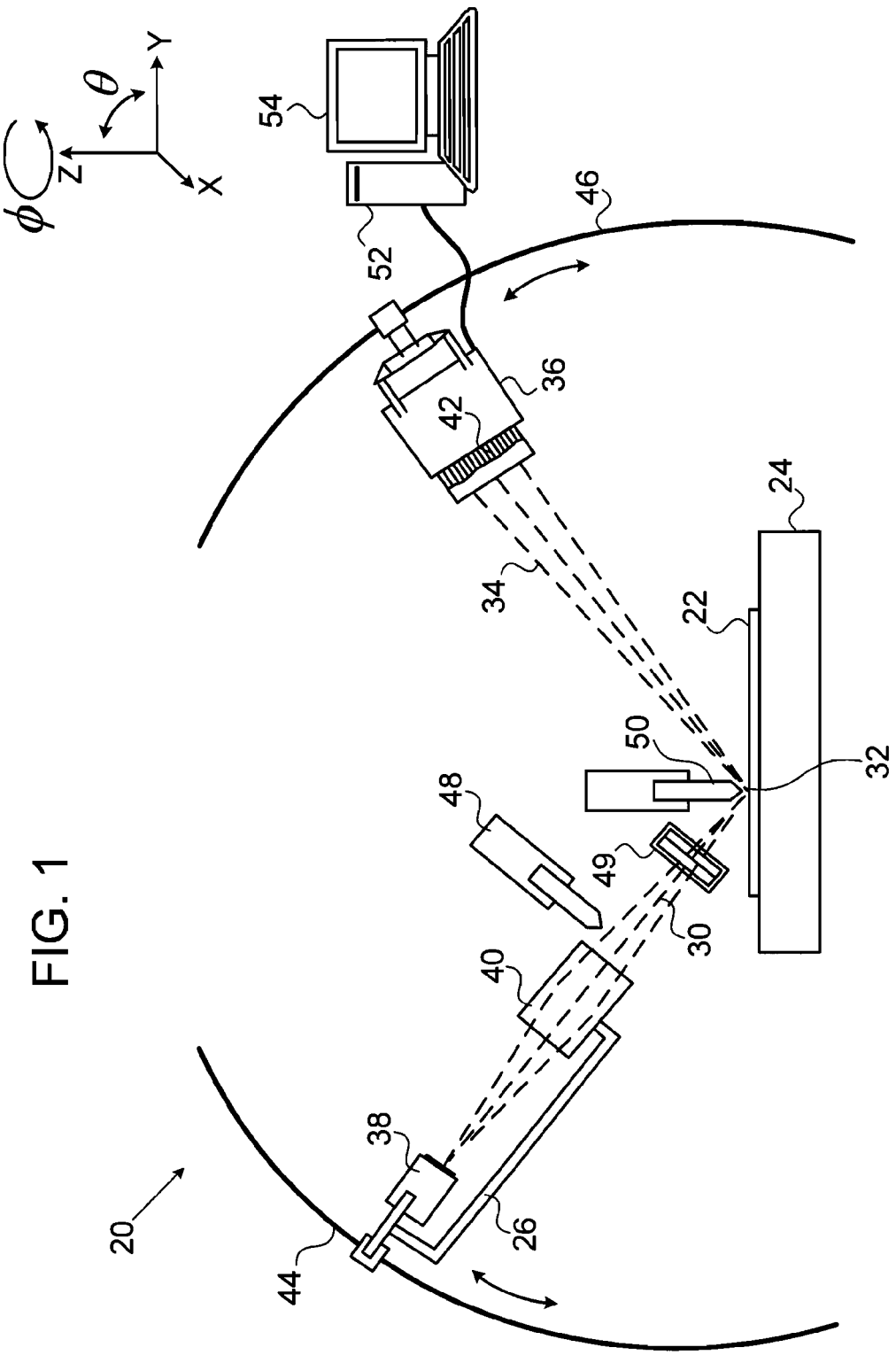
FIG. 1 is a schematic side view of a system for high-resolution X-ray diffraction (HRXRD) measurement, in accordance with an embodiment of the present invention.

Embodiments of the present invention that are described hereinbelow provide enhanced methods and systems for analysis of crystalline samples using high-resolution X-ray diffraction (HRXRD). The disclosed embodiments afford enhanced accuracy in characterizing thin-film epitaxial layers, and are thus particularly useful in testing and monitoring the production of semiconductor devices. The principles of the present invention, however, may similarly be applied in studying and characterizing samples of other kinds.

In the disclosed embodiments, a converging beam of X-rays is directed toward a surface of a sample, which typically includes multiple crystalline layers (for example, a silicon substrate with an epitaxial doped layer, such as SiGe, formed on the surface). A detector assembly, which typically comprises a detector array, senses the X-rays that are diffracted from the sample while resolving the sensed X-rays as a function of angle. The detector assembly thus captures a diffraction spectrum, which typically includes a respective diffraction peak due to each of the layers, and possibly weaker features, as well, such as a fringe pattern. The separation between the peaks is often indicative of the composition of the layers, such as the concentration of the germanium dopant in the SiGe layer. The fringe pattern can provide information on physical dimensions of the crystalline layer structure.

The diffraction peak due to one or the layers, such as the peak arising from the substrate of the sample, is often strong and may tend to hide or wash out the weaker features. Therefore, in some embodiments, a beam blocker is introduced into the converging beam so as to block a range of angles containing the strong diffraction peak. The resulting diffraction spectrum permits the weaker features, such as the above-mentioned fringe pattern, to be measured with greater accuracy. Methods for facilitating accurate placement of the beam blocker are described hereinbelow.

Relaxation of epitaxial layers, in which the crystalline structure of a thin-film layer comes out of alignment with the substrate (or other layer) below it, can cause defects in semiconductor devices containing these layers. It is therefore important to detect relaxation and to make process adjustments, if required, to reduce relaxation in subsequently-manufactured wafers. In some embodiments of the present invention, grazing-angle asymmetric HRXRD is used to measure relaxation. In another embodiment, the amplitude of the fringes in the diffraction spectrum provides a measure of relaxation. Typically, a reduction in the fringe amplitude is indicative of an increase in the relaxation.

Normally, the X-ray source and sample are positioned so that the converging beam of X-rays is focused to a spot on the sample. The inventors have discovered, however, that shifting the sample out of the focus when operating in asymmetric mode can increase the separation between the peaks in the diffraction spectrum. (In asymmetric mode, the X-rays are diffracted from the sample at takeoff angles that are different from the incidence angles, in contrast to the symmetric mode, in which the incidence and takeoff angles are the same.) Therefore, in some embodiments, the sample is intentionally positioned out of focus, in order to permit more accurate measurement of secondary peaks and other weak features in the spectrum. Furthermore, the relative shift between the peaks as a function of the distance of the sample from the focus can be measured to provide useful information regarding an epitaxial layer on the sample, such as the concentration of a dopant in the layer.

Additionally or alternatively, while the sample is out of focus and the diffraction peaks are far apart, a beam blocker can be precisely positioned to block a strong peak, such as the substrate peak, after which the sample may be shifted back into focus.

In asymmetric mode, the X-ray beam may be incident on the sample at a grazing angle, or the diffracted X-ray beam may be detected at a grazing angle. The term "grazing angle," in the context of the present patent application, means an angle that is close to the surface of the sample, typically within 10° of the surface. Grazing angle measurements are useful in detecting diffraction from crystal planes that are not parallel to the sample surface and may be used, for example, to measure relaxation of an epitaxial layer. They have the disadvantage, however, that the spot area from which diffraction is detected is elongated along the beam axis, and diffraction measurements made on small features may consequently be distorted. To alleviate this problem, in some embodiments of the present invention, a beam limiter is positioned to block a portion of the X-rays in a location adjacent to the spot on the sample. The beam limiter reduces the dimension of the spot along the beam axis direction and thus can improve measurement accuracy.

System Description

FIG. 1 is a schematic side view of a system 20 for HRXRD of a sample 22, in accordance with an embodiment of the present invention. In the embodiments that are described hereinbelow, sample 22 is taken to be a silicon wafer on which an epitaxial layer is deposited, and the HRXRD capabilities of system 20 are applied in analyzing characteristics of the epitaxial layer. In alternative embodiments, however, system 20 may be used to analyze crystalline samples of other types. Additionally or alternatively, system 20 may be configured to carry out other types of X-ray measurements, such as measurements of X-ray reflectometry (XRR), X-ray fluorescence (XRF), and small-angle X-ray scattering (SAXS), as described, for example, in U.S. Pat. Nos. 7,120,228 and 7,551,719, whose disclosures are incorporated herein by reference.

In system 20, sample 22 is mounted on a motion device, such as a motion stage 24, allowing accurate adjustment of the position and orientation of the sample. Alternatively or additionally, the motion device may shift and adjust other elements of the system relative to the sample. An X-ray source 26 directs a converging X-ray beam 30 onto a spot 32 on sample 22. Generally, source 26 and stage 24 are adjusted so that the focus of beam 30 is located precisely at spot 32 on the sample surface, but in some cases (as described in greater detail hereinbelow), the sample height (Z-coordinate) may be shifted out of the beam focus. A detector assembly 36 detects a diverging beam 34 of X-rays that is diffracted from the sample.

Typically, source 26 comprises an X-ray tube 38 with suitable optics 40 to focus and monochromatize beam 30. Beam 30 typically subtends at least 2°, and may subtend as much as 4° or even more, depending on optics 40, in order to irradiate sample 22 over a large range of angles simultaneously. Optics 40 may comprise, for instance, a curved crystal monochromator, which focuses and monochromatizes an input beam from tube 38. Further details of X-ray tubes and optics that may be used in this context are described, for example, in the above-mentioned U.S. Pat. Nos. 7,120,228 and 7,551,719, as well as in U.S. Pat. No. 7,076,024, whose disclosure is incorporated herein by reference.

Detector assembly 36 typically comprises a detector array 42, such as a CCD array, comprising multiple detector elements, configured so as to resolve beam 34 as a function of elevation angle θ. Detector assemblies of this type are also described in the above-mentioned patents. Typically, the angular span of array 42 is comparable to that of beam 30, i.e., at least 2°, and possibly 4° or greater. A beam blocker 48 and a beam limiter 50 (such as a knife edge) and/or other optical elements may be used to limit beam 30 and/or beam 34 and to block undesired scattered radiation that might otherwise strike array 42 and interfere with the diffraction measurement. Another beam blocker 49, oriented perpendicularly to blocker 48, is used to block undesired irradiation wavelengths. The use of these elements in enhancing HRXRD measurements is described in greater detail hereinbelow.

Figure 2:
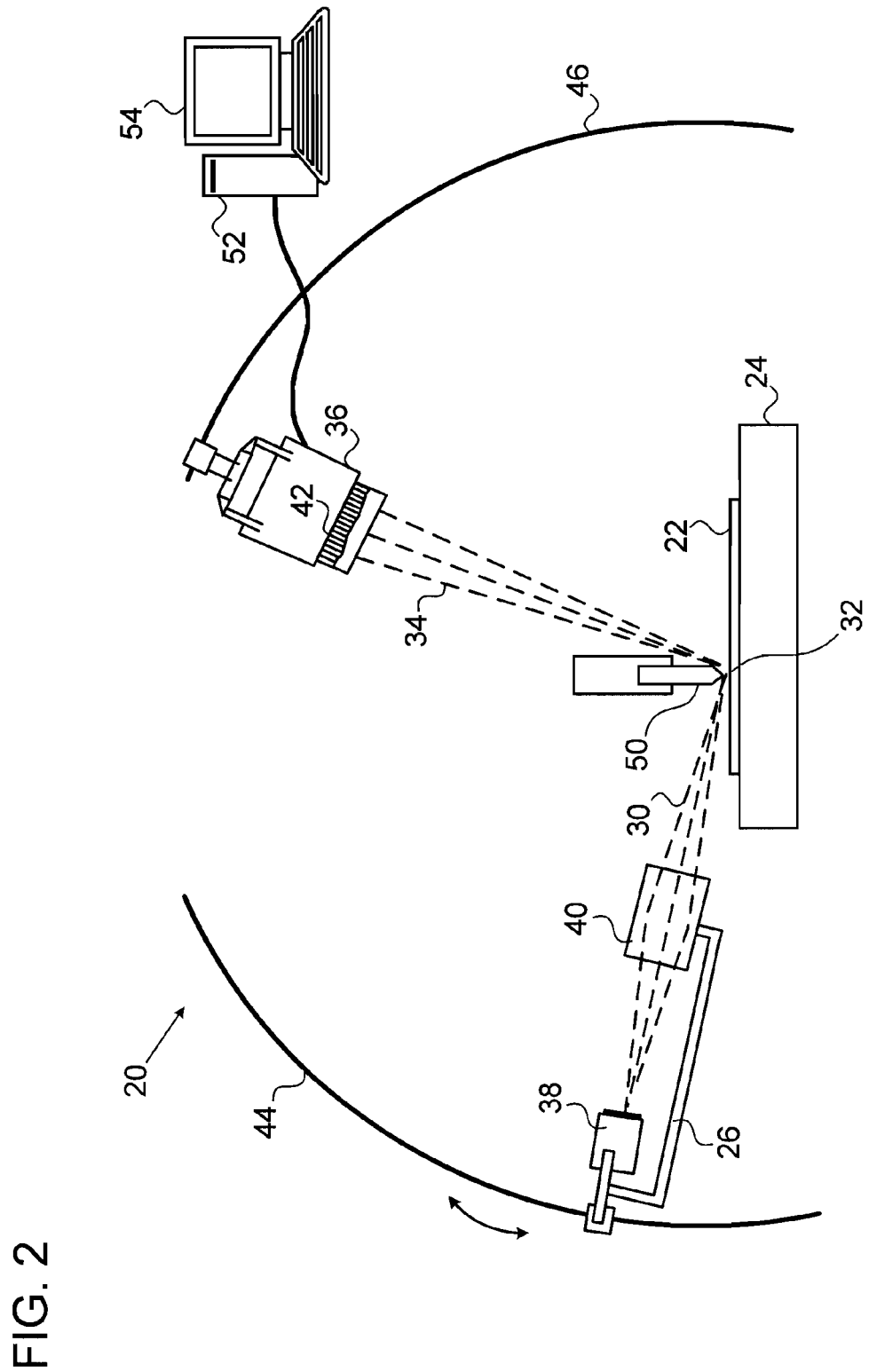
FIG. 2 is a schematic side view of the system of FIG. 1 in an alternative configuration, in accordance with an embodiment of the present invention.

The positions of source 26 and detector assembly 36 are controlled by motion assemblies 44 and 46, respectively. In the simplified view shown in FIG. 1, the motion assemblies comprise curved tracks, which permit the source and detector assembly to be positioned at the appropriate elevations, typically in the vicinity of the Bragg angles of the layers that are to be analyzed. Other suitable motion assemblies may alternatively be used, as will be apparent to those skilled in the art. For the sake of the example shown in FIG. 1, it is assumed that the lattice planes creating the diffraction pattern of interest are approximately parallel to the surface of sample 22, so that the incidence and takeoff angles defined by beams 30 and 34 relative to the surface are both equal to the Bragg angle. (This assumption is often true with respect to semiconductor substrates, such as silicon wafers, and epitaxial layers that are grown on such substrates.) Alternatively, source 26 and detector assembly 36 may be positioned at different incidence and takeoff angles, as shown in FIG. 2, for example, in order to measure diffraction from lattice planes that are not parallel to the surface of sample 22.

In a typical embodiment, as noted above, stage 24 is configured to translate the height (Z-coordinate) of sample 22 and the X-Y location on the sample that falls within spot 32, as well as to rotate the azimuthal angle Φ and incidence angle of the sample relative to beam 30. (As shown in FIG. 1, the X-Y plane is taken to be the sample surface, with the Z-axis perpendicular to the surface; θ is the elevation angle relative to the Z-axis; and Φ is the azimuthal angle of rotation about the Z-axis.) Additionally or alternatively, these position and angle adjustments may be achieved by moving or otherwise adjusting other elements of system 20, such as the source and detector assemblies.

A signal processor 52 receives and analyzes the output of assembly 36, so as to measure a spectrum 54 of the flux of X-ray photons diffracted from sample 22 as a function of elevation angle θ at a given energy or over a range of energies. Typically, spectrum 54 as a function of elevation angle exhibits a structure that is characteristic of diffraction effects due to the surface layer and underlying layers, including the sample substrate. Processor 52 analyzes the angular spectrum in order to identify characteristics of one or more of the layers of the sample, such as the composition, lattice strain (or equivalently, relaxation) and/or tilt angle of a given layer, using methods of analysis described hereinbelow.

As noted above, the components of system 20 and the techniques described herein may be used to provide other types of measurement functionality, such as X-ray reflectometry and scattering measurements. Additionally or alternatively, these components and techniques may be integrated as process monitoring tools in manufacturing systems, such as systems for semiconductor wafer fabrication. For example, in an alternative embodiment of the present invention (not shown in the figures), elements of system 20 are integrated with a semiconductor wafer fabrication tool to provide in situ inspection. Typically, the fabrication tool comprises a vacuum chamber containing deposition apparatus for creating thin films on a wafer, as is known in the art. The chamber has X-ray windows, as described, for instance, in U.S. Patent Application Publication US 2001/0043668, now U.S. Pat. No. 6,970,532, whose disclosure is incorporated herein by reference. X-ray source assembly 26 may then irradiate spot 32 on the wafer via one of the windows, and detector assembly 36 may receive the scattered X-rays through another window. In another alternative embodiment, system 20 may be configured as a station in a cluster tool, along with other stations used in performing production steps.

FIG. 2 is a schematic side view of system 20 in an alternative, asymmetric configuration, in accordance with an embodiment of the present invention. In this case, source 26 is positioned by motion assembly 44 so as to irradiate sample 22 at a grazing angle, with the central beam axis 8° from the sample surface, for example. Motion assembly 46 positions detector assembly 36 at a high angle, for example, 79°, in order to capture Bragg diffraction from lattice planes that are not parallel to the sample surface. This configuration is useful in measuring the spacing between cells of the crystal lattice along the direction parallel to the sample surface and can thus be used in assessing relaxation of epitaxial layers (as illustrated below in FIGS. 5A and 5B).

In an alternative embodiment, not shown in the figures, beam 30 may irradiate the sample surface at a high angle, while detector assembly 36 is positioned to capture X-rays diffracted from the sample at grazing angles.

Enhancement of Resolution by Use of Beam Blockers

Figure 3A:
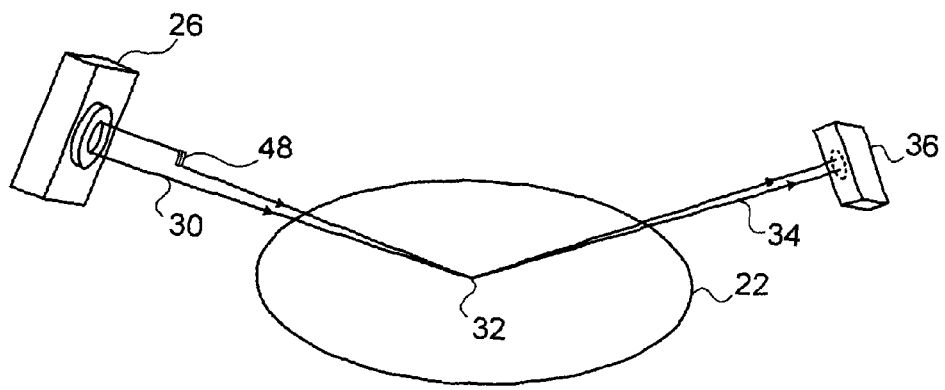
FIG. 3A is a schematic, pictorial illustration of elements of a HRXRD system, showing the use of a beam blocker in accordance with an embodiment of the present invention.

FIG. 3A is a schematic, pictorial illustration of elements of HRXRD system 20, showing the use of beam blocker 48 in accordance with an embodiment of the present invention. In the default position, the beam blocker is retracted, as shown in FIG. 1, and does not impinge on incident beam 30. In some circumstances, however, it is advantageous to block a certain angular range within the beam. Beam blocker 48 may be positioned to block an upper portion of the range, as illustrated in FIG. 3A, or it may alternatively be positioned to block a lower portion. The corresponding range of angles in diffracted beam 34 will similarly be cut off, or at least attenuated. This application of the beam blocker is useful in attenuating intense components of the diffraction spectrum, in order to reduce the dynamic range of the diffracted beam and facilitate detection of weak features that might otherwise be washed out.

Figure 3B:
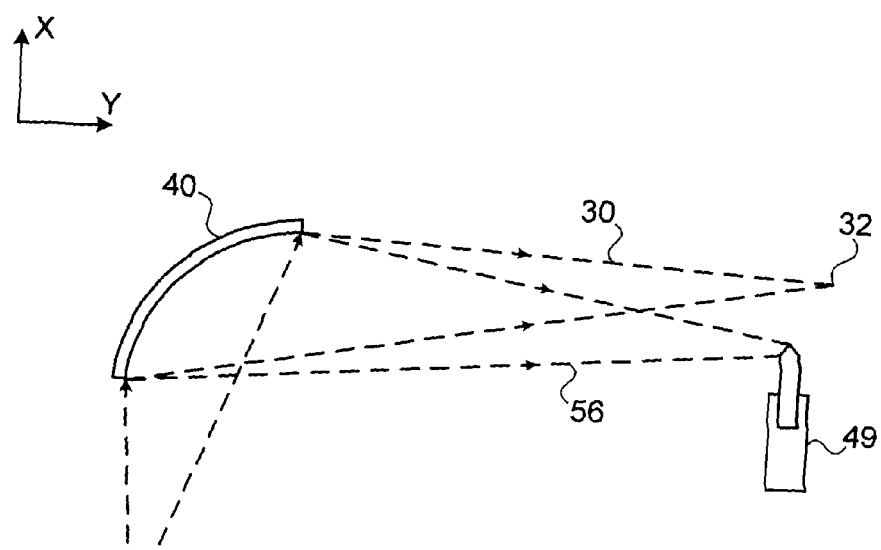
FIG. 3B is a schematic top view of elements of a HRXRD system, showing the use of a beam blocker in accordance with another embodiment of the present invention.

FIG. 3B is a schematic top view of elements of HDXRD system 20, showing the use of beam blocker 49 in accordance with an embodiment of the present invention. X-ray tube 38 typically emits multiple X-ray wavelengths, which may be closely spaced, such as the Cu Kα1 and Kα2 wavelengths. Optics 40 (shown in this figure as a curved crystal monochromator) may not fully filter out nearby emission lines. Thus, in the present example, when beam 30 comprises the Cu Kα1 line, optics 40 also focus the Cu Kα2 line from tube 38 into an adjacent beam 56. In a typical configuration of system 20, the focus of beam 56 is only slightly displaced, by less than 1 mm, and in some cases less than 0.2 mm, from focal spot 32 of beam 30. (The separation between the beams is exaggerated in the figure for the sake of clarity.) Scattered Cu Kα2 radiation may therefore reach detector assembly 36 and interfere with the HDXRD measurement.

Beam blocker 49 can be used to alleviate this problem. This beam blocker may comprise, for example, a metal knife edge oriented in the vertical (Z) direction. The knife edge is adjusted, as shown in FIG. 3B, to block beam 56 at a location a few millimeters before the focus. Beam 56 is well separated from beam 30 at this location, and beam blocker 49 thus does not intercept the desired beam 30.

Figure 4:
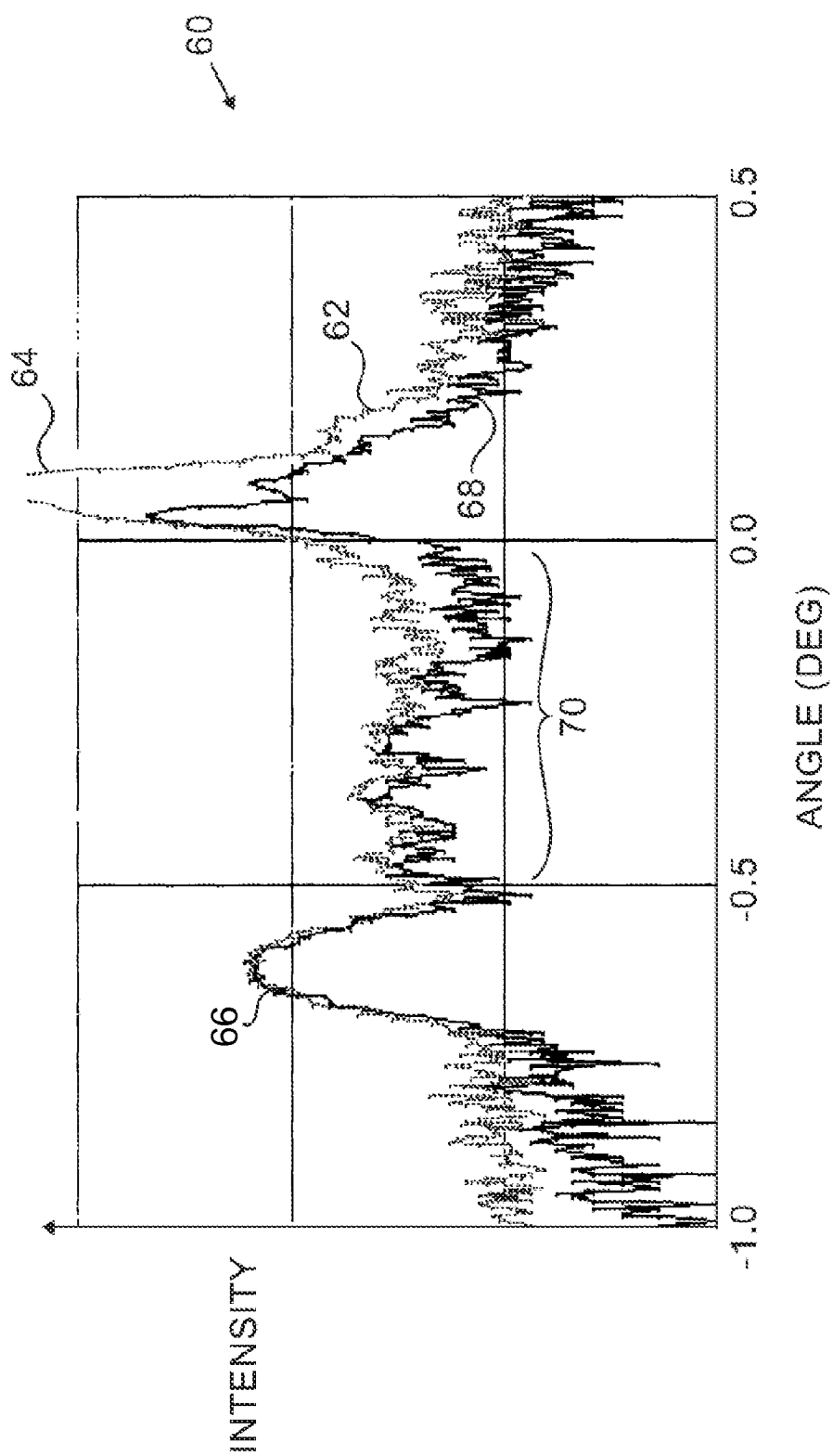
FIG. 4 is a plot that schematically shows HRXRD spectra taken at different positions of a beam blocker, in accordance with an embodiment of the present invention.

FIG. 4 is a plot 60 that schematically shows HRXRD spectra taken at different positions of beam blocker 48, in accordance with an embodiment of the present invention. An unblocked spectrum 62, with the beam blocker withdrawn from beam 30, is dominated by a substrate peak 64, due to Bragg diffraction from the silicon substrate of the wafer under test. In this example, an epitaxial SiGe layer has been formed on the substrate, and spectrum 62 includes a side peak 66 due to Bragg diffraction from the SiGe layer. (The angular separation between peaks 64 and 66 is indicative of the concentration of the germanium dopant in the SiGe.) A fringe structure 70 in the intermediate angular region between peaks 64 and 66, however, is difficult to see in spectrum 62 because of the spread of radiation from peak 64 into this region.

To alleviate this problem, once the location of peak 64 has been ascertained in spectrum 62, beam blocker 48 is positioned to block the corresponding range of angles in incident beam 30. The beam blocker is positioned precisely in order to minimize blockage of the of the intermediate region that contains fringe structure 70. In a resulting blocked spectrum 68 in FIG. 4, peak 64 is largely suppressed, and the resolution of the fringe structure is therefore enhanced. The period and amplitude of this fringe structure can provide valuable information regarding the dimensions of the epitaxial layer.

In one embodiment, processor 52 controls beam blocker 48 on the basis of spectrum 62. The processor analyzes the spectrum in order to find the location and width of peak 64. The processor then computes the desired position of the beam blocker in order to attenuate peak 64 and outputs a control signal to the beam blocker accordingly. The beam blocker typically comprises a motion control device, such as a motor with linear encoder, which is actuated to position the beam blocker according to the signal from processor 52.

Although the use of beam blocker 48 is illustrated in FIGS. 1 and 3A in the symmetric diffraction mode, the beam blocker may be used in like manner for the same purpose in the asymmetric mode that is shown in FIG. 2.

Measurement of Relaxation of Epitaxial Layers

Figure 5B:
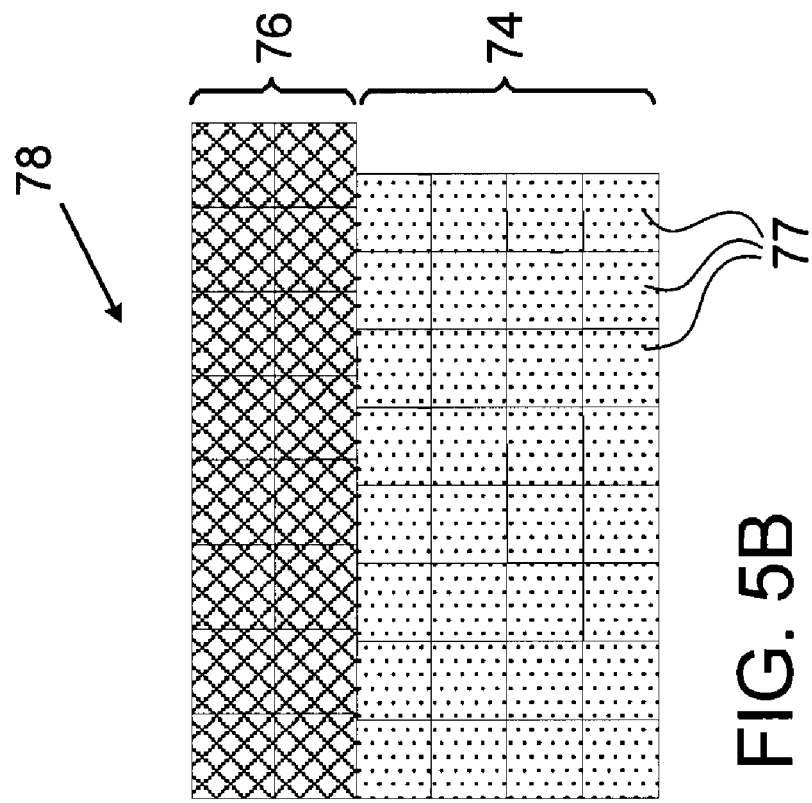
FIGS. 5A and 5B are schematic, sectional views of an epitaxial layer on a substrate in pseudomorphic and relaxed configurations, respectively.
Figure 5A:
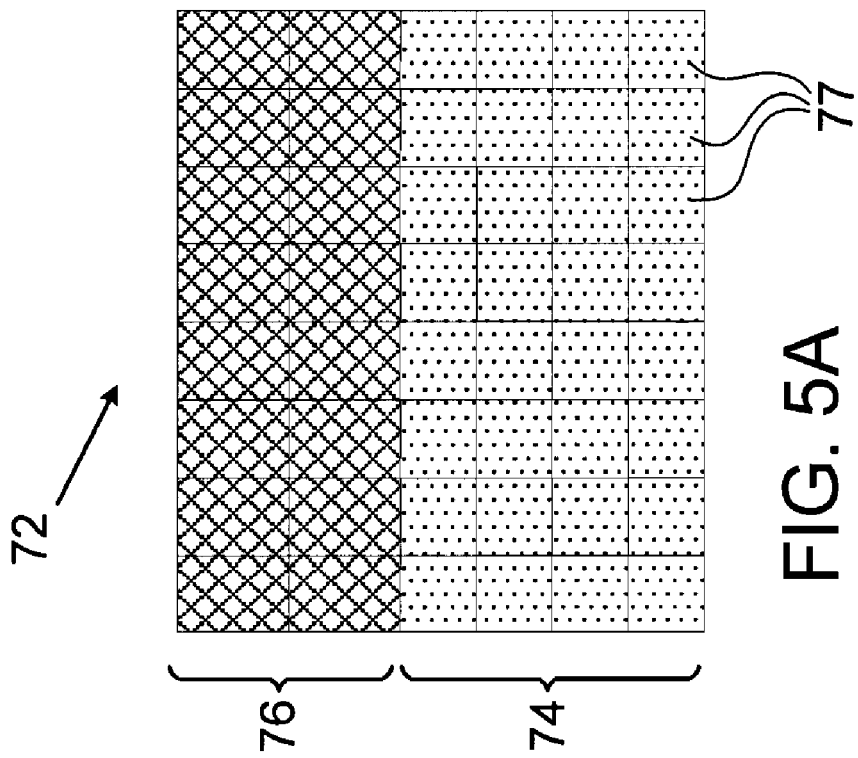

FIGS. 5A and 5B are schematic, sectional views of samples 72 and 78, respectively, in which an epitaxial layer 76 has been formed on a substrate 74. Layer 76 may comprise, for example, a thin film of SiGe that is formed on a silicon substrate. The addition of the germanium dopant causes unit cells 77 in layer 76 to be larger in volume than the unit cells of substrate 74. (The difference is exaggerated in the figures for the sake of visual clarity.) In sample 72, layer 76 is pseudomorphic, meaning that the unit cells in layer 76 are strained so as to maintain alignment with the underlying cells of layer 74. In sample 78, however, cells 77 in layer 76 have relaxed to a cubic configuration and have lost alignment with the underlying cells. This sort of relaxation, which may result from improper settings in the manufacturing process, can cause defects in semiconductor devices that are made from this wafer. It is therefore important to monitor relaxation of epitaxial layers and to adjust the process appropriately when relaxation is detected.

One method for monitoring relaxation is to measure changes in the relative positions of the diffraction peaks dues to the substrate and to the layer in question in asymmetric measurement mode. An alternative method, which may provide more accurate results, is to analyze the fringe structure in the diffraction spectrum.

Figure 6:
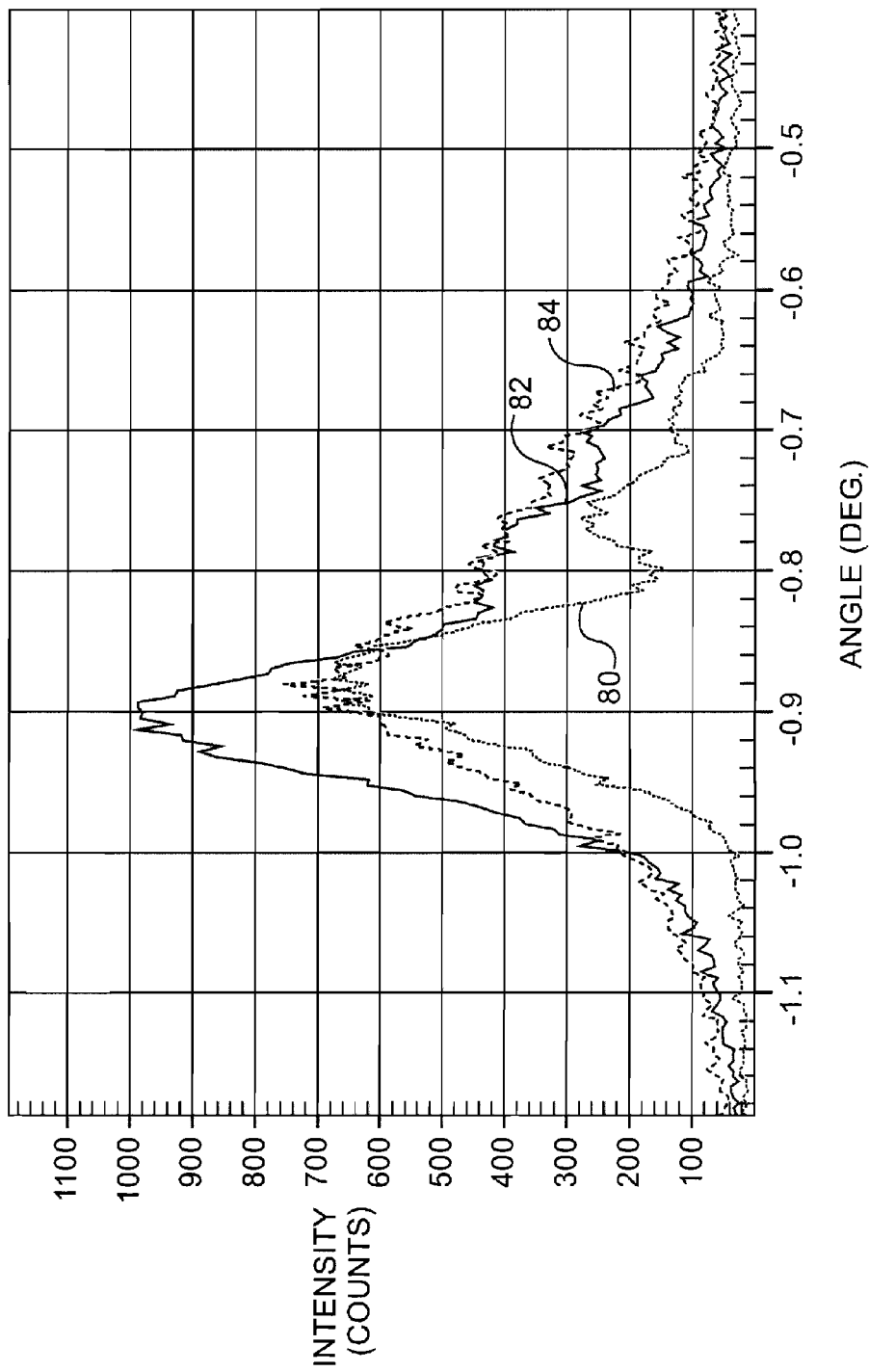
FIG. 6 is a plot that schematically shows HRXRD spectra measured in accordance with an embodiment of the present invention, at different degrees of relaxation of an epitaxial layer.

FIG. 6 is a plot that schematically shows HRXRD spectra 80, 82 and 84, illustrating the effect of relaxation of an epitaxial layer on the fringe structure, in accordance with an embodiment of the present invention. The spectra were taken in symmetric mode from SiGe layers formed on a silicon substrate. The strong peaks due to the substrate have been blocked out of these spectra, as explained above.

Spectrum 80 was taken from a fully-strained SiGe layer. The fringes between the angles of about −0.55° and 0.85° are clearly visible and have a large amplitude, on the order of 100 counts. On the other hand, there are no visible fringes at all in spectrum 84, which was taken from a fully-relaxed layer (with a dimensional shift of approximately 6.6% between unit cells of the SiGe layer and those of the underlying silicon). In the intermediate example of spectrum 82, the SiGe layer is mildly relaxed (dimensional shift of approximately 3%), and the fringes are visible but with much-reduced amplitude.

Based on these findings, processor 52 may analyze fringe amplitudes in HRXRD spectra in order to estimate the extent of relaxation of epitaxial layers. The amplitude of the fringes may be extracted by parametric fitting of the spectrum to a model, and the resulting fit parameters will give an accurate indication of the layer relaxation. The period of the fringes is indicative of the thickness of the epitaxial layer.

Enhancing Detection Accuracy in Asymmetric Mode

Figure 7:
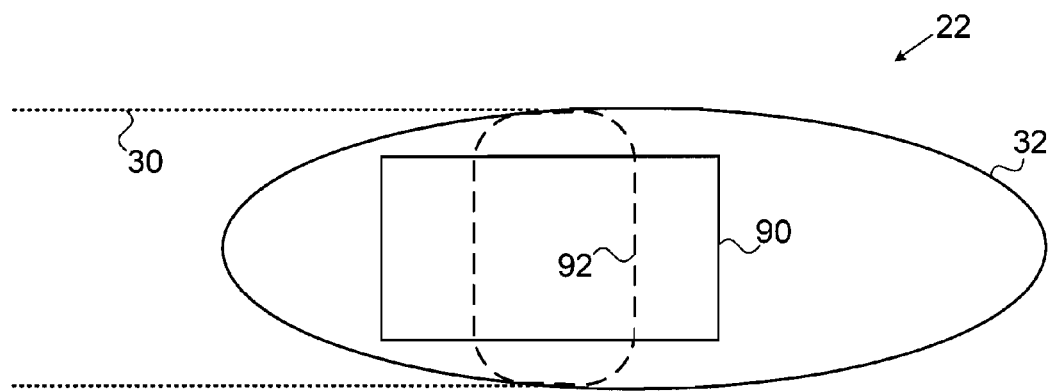
FIG. 7 is a schematic top view of a sample showing incidence of an X-ray beam on the sample in different beam-spread conditions, in accordance with an embodiment of the present invention.
Figure 8:
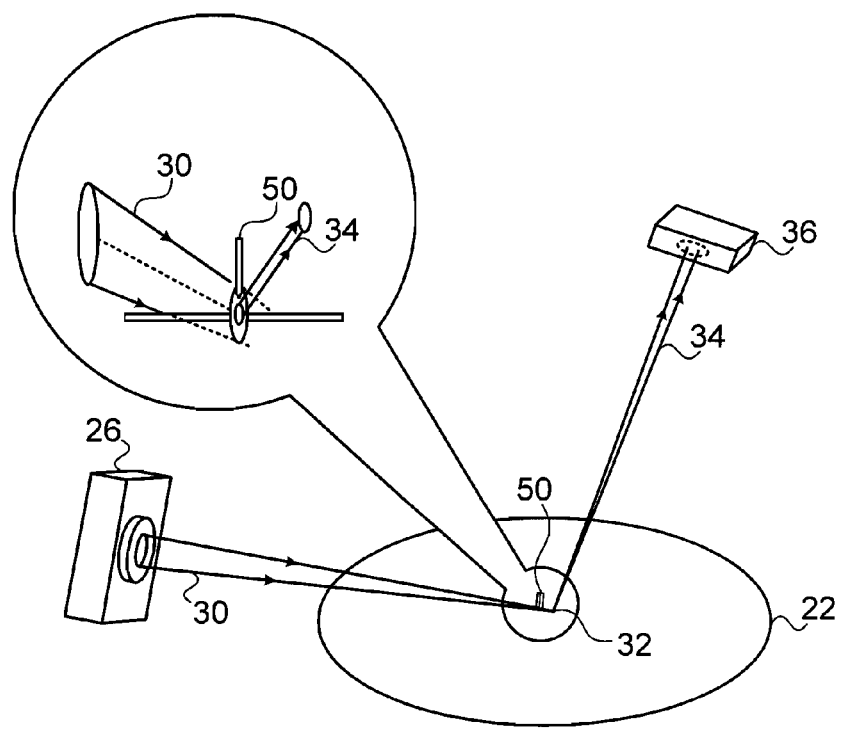
FIG. 8 is a schematic, pictorial illustration of elements of a HDXRD system, showing the use of a beam limiter to control beam spread in accordance with an embodiment of the present invention.

Reference is now made to FIGS. 7 and 8, which schematically illustrate the use of beam limiter 50 in asymmetric-mode HRXRD in system 20, in accordance with an embodiment of the present invention. FIG. 7 is an enlarged top view of sample 22, showing spot 32 formed by X-ray beam 30 on the sample and the effect of beam limiter 50 on the extent of the spot. FIG. 8 is a pictorial illustration of elements of system 20 showing how beam limiter 50 (an adjustable knife edge in this embodiment) is inserted into beam 30 in order to control the extent of the spot on the sample. Although FIG. 8 shows a configuration in which incident beam 30 impinges on sample 22 at grazing incidence, the beam limiter may similarly be used in the alternative configuration in which the diffracted beam takes off from the sample at a grazing angle. The problem addressed by the beam limiter is less acute in this alternative configuration, but it may still be desirable to limit the extent of the spot.

In FIG. 7, an epitaxial layer is formed as a small pad 90 on the surface of sample 22. Because of the low incidence angle of beam 30, spot 32 extends over pad 90 and also covers a large area of the substrate that is not covered by the epitaxial layer. The mismatch between spot 32 and pad 90 has at least two undesirable consequences:
1) The strong peak in the HRXRD spectrum due to the substrate (peak 64 in FIG. 4) will be enhanced relative to peak 66 and to other spectral structure originating from the epitaxial layer.
2) The displacement of pad 90 relative to the center of spot 32 on sample 22 will distort the apparent angular separation between layer peak 66 and substrate peak 64 in the XRD spectrum.

To alleviate these problems, beam limiter 50 is inserted into beam 30 above spot 32. When a knife edge is used for beam limiting, for example, the knife edge is lowered to a small distance above the surface of sample 22, so as to block the upper portion of beam 30 and also to block diffracted rays resulting from the lower portion of beam 30, as illustrated in the inset in FIG. 8. In a typical configuration, the knife edge is positioned on the order of 15 μm above the sample surface, but larger or smaller distances may be used depending on application requirements. As a result of the beam limiter, the effective size of the irradiating beam is reduced, so that detector assembly 36 receives diffracted X-rays only from a reduced spot 92. The dimension of spot 92 in this example is reduced in the Y-direction (the direction of the projection of the axis of beam 30 onto the sample surface), so that spot 92 falls almost entirely on pad 90. As a result, the relative strength of layer peak 66 is enhanced in the diffraction spectrum, and the distortion in the separation between substrate peak 64 and layer peak 66 is eliminated.

Figure 9:
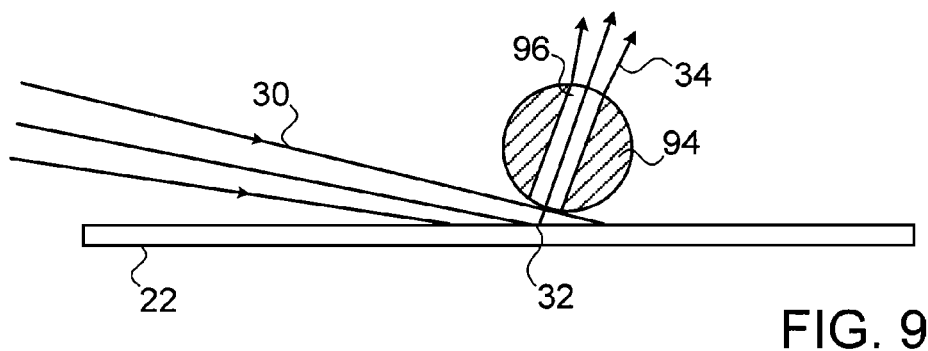
FIG. 9 is a schematic, sectional view of a beam limiter, in accordance with another embodiment of the present invention.

FIG. 9 is a schematic, sectional view of a beam limiter 94, in accordance with another embodiment of the present invention. The beam limiter in this embodiment may be made, for example, from a metal rod having a cylindrical profile, as shown in the figure, or any other suitable profile. A hole 96 through the rod reduces the effective size of spot 32 by geometrically limiting the area from which diffracted X-rays in beam 34 are allowed to reach the detector assembly. Incident beam 30 impinges on sample 22 below beam limiter 94 at a grazing angle, such as 8°, while diffracted beam 34 leaves the sample at about 79° through hole 96. The beam limiter may be about 0.4 mm in diameter, with a hole having a diameter of about 40 μm, but larger or smaller holes may be used depending on the desired spatial resolution.

Beam limiter 94 may likewise be used in asymmetric grazing exit mode, in which sample 22 is irradiated at a high angle and the diffracted beam is detected at grazing angles. In this case, the beam limiter is placed in incident beam 30, so that the incident X-rays pass through hole 96, thus defining and limiting the spot from which the X-rays are diffracted.

Figure 10:
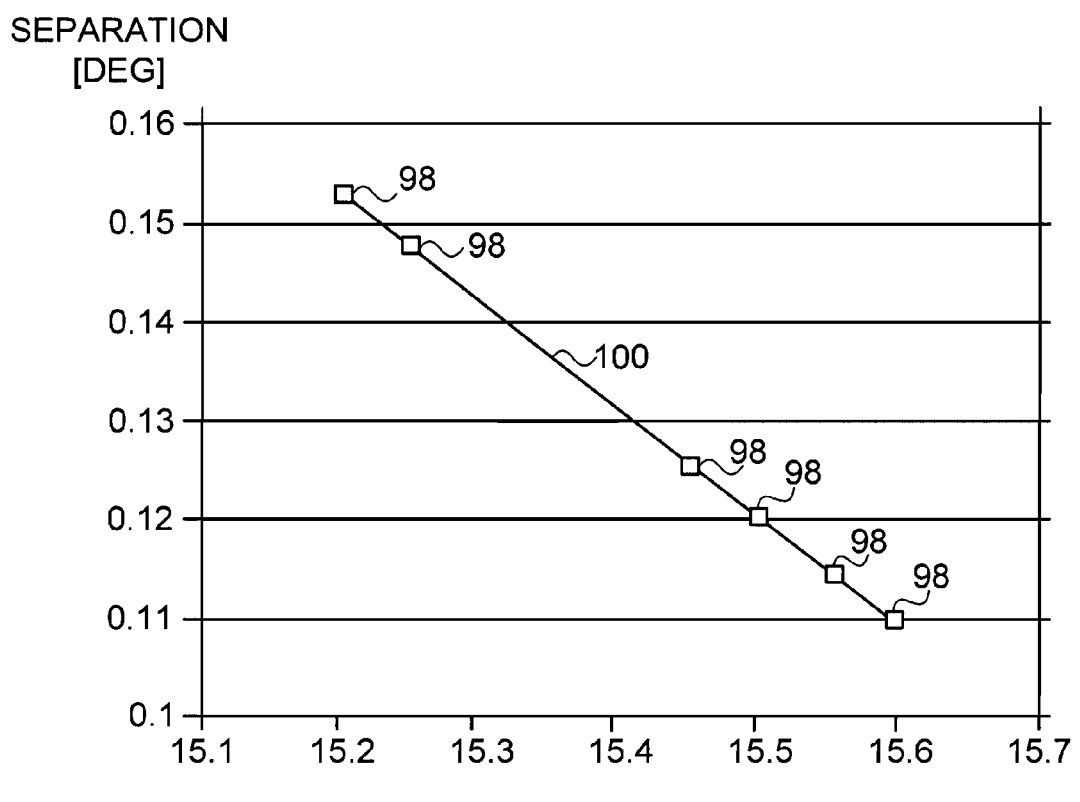
FIG. 10 is a plot that schematically shows a dependence of characteristics of a HRXRD spectrum on sample height, in accordance with an embodiment of the present invention.

FIG. 10 is a plot that schematically shows a dependence of characteristics of a HRXRD spectrum on sample elevation, in accordance with an embodiment of the present invention. Data points 98 in this plot correspond to the separation between substrate peak 64 and layer peak 66 (as shown in FIG. 4) due to an epitaxial layer of SiGe, measured in asymmetric diffraction mode as a function of the height (Z-coordinate) of the silicon wafer. The Z-coordinate is taken to be the direction perpendicular to the sample surface and is controlled by stage 24, as shown above in FIGS. 1 and 2. Changing the Z-coordinate moves the sample surface in and out of the focus of incident beam 30. The lateral (Y-coordinate) position of the spot is held effectively constant on the wafer, however, in order to avoid changes in peak separation due to the sort of spot displacement that is illustrated in FIG. 7 and explained above. As the surface of the wafer moves out of the beam focus (lower values of Z in FIG. 10), the apparent separation between peaks 64 and 66 increases. The increase is linear with the displacement from the focus (i.e., with Z), as shown by a line 100 that is fitted to the data.

The phenomenon illustrated in FIG. 10 has a number of useful applications. For purposes of these applications, the parameters of line 100 may be pre-calibrated using one or more samples of known characteristics. For example, the slope and intercept of the line may be calibrated using samples with epitaxial layers having different, known dopant concentrations and degrees of relaxation. The HRXRD peak separation at different sample heights may then be measured for a sample under test, and the sample characteristics—dopant concentration and relaxation of the epitaxial layer—may be ascertained based on the slope (and possibly the intercept) of the peak separation as a function of the height. Alternatively, in order to measure the dopant concentration, the peak separation may first be measured in symmetric mode (in which the separation is not sensitive to sample height), and the variation of peak separation with height in asymmetric mode may then be used to measure relaxation.

In another embodiment, the sample in asymmetric mode may be positioned intentionally at a height that is out of the focus of incident beam 30 in order to increase the separation between peaks 64 and 66. Increasing the peak separation may be useful in enhancing the visibility of fine details associated with an epitaxial layer, such as fringe structure 70 in the intermediate region between the peaks.

As another alternative, the increased peak separation when sample 22 is moved out of focus may be used to facilitate placement of beam blocker 48 (as shown in FIG. 3A). The beam blocker is positioned precisely to block substrate peak 64 at the out-of-focus position of the sample, so that peak 64 is entirely blocked while minimizing blockage of the spectral structure near the peak. The sample may then be moved back into the focal position, while the position of the beam blocker relative to incident beam 30 remains unchanged. This procedure may be carried out automatically, under the control of processor 52.

Reciprocal Space Mapping

Figure 11:
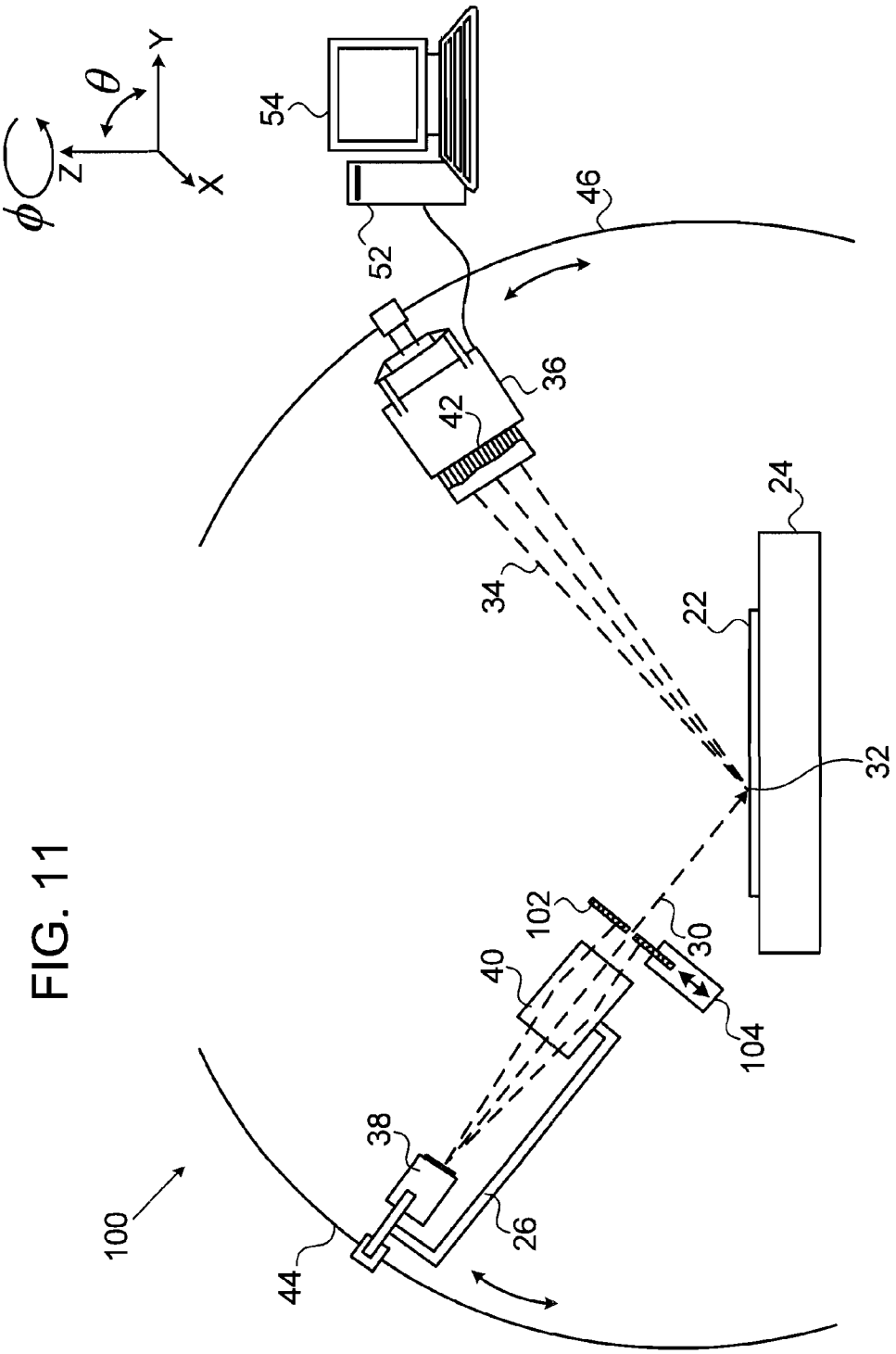
FIG. 11 is a schematic side view of a system for HRXRD measurement, in accordance with another embodiment of the present invention.

FIG. 11 is a schematic side view of a system 100 for HRXRD measurement, in accordance with another embodiment of the present invention. System 100 is similar in most respects to system 20, and the features shown in FIG. 11 may, optionally, be integrated into system 20. The description that follows will therefore focus only on the specific elements of system 100 that are used in creating a reciprocal space map (RSM) and the method of their use for this purpose. RSM is a technique that is known generally in the art, as described, for example, by Woitok and Karchenko in "Towards Fast Reciprocal Space Mapping," *Advances in X-ray Analysis* 48, pages 165-169 (2005), which is incorporated herein by reference. The embodiment shown in FIG. 11, however, offers advantages of fine spatial resolution (on the order of 60 μm) and rapid data collection.

In the present embodiment, a slit 102, oriented in the X-direction, limits converging beam 30 to a narrow range of angles. A scanning mechanism 104, such as a precision motorized drive, scans the slit across beam 30. Thus, each of a sequence of angles of incidence within the angular range of beam 30 is sampled individually, rather than sampling the entire range at once as in the embodiment of FIG. 1. For each incident angle, detector assembly 36 senses the diffracted X-ray intensity in beam as a function of angle over the entire range of takeoff angles that is received by detector array 42.

In this manner, processor 52 collects a three-dimensional (3D) dataset, containing the measured diffraction intensity for each incident/takeoff angle pair. The processor may present these data as a 3D plot, which is known as a reciprocal space map. This sort of presentation is useful in analysis of certain types of complex crystalline structures, such as when the surface of sample 22 is geometrically distorted.

Although the methods described above relate, for the sake of clarity, specifically to the elements of system and to a certain type of silicon wafer sample and epitaxial layer, the principles of these methods may similarly be applied to other types of samples and in other HRXRD system configurations. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for analysis, comprising:
directing a converging beam of X-rays toward a surface of a sample having first and second crystalline layers, with different, respective crystal characteristics;
sensing the X-rays that are diffracted from the sample while resolving the sensed X-rays as a function of angle so as to generate a first diffraction spectrum comprising at least a first diffraction peak due to the first layer and a second diffraction peak due to the second layer;
positioning a beam blocker in the converging beam so as to block a range of angles in the converging beam that corresponds to the first diffraction peak;
sensing the X-rays that are diffracted from the sample while the beam blocker is positioned in the converging beam so as to generate a second diffraction spectrum comprising at least the second diffraction peak while the first diffraction peak is at least partly blocked; and
analyzing at least the second diffraction spectrum so as to identify a characteristic of at least the second layer.

2. The method according to claim 1, wherein sensing the X-rays comprises deploying a detector array having elements configured to capture and resolve the X-rays over a range of elevation angles simultaneously.

3. The method according to claim 2, wherein the range is at least 2 degrees.

4. The method according to claim 1, wherein the second layer is deposited epitaxially over the first layer.

5. The method according to claim 4, wherein the first layer comprises a semiconductor substrate, and the second layer comprises a doped semiconductor.

6. The method according to claim 5, wherein the semiconductor substrate comprises a silicon wafer, and the second layer comprises a SiGe epitaxial layer.

7. The method according to claim 1, wherein analyzing at least the second diffraction spectrum comprises analyzing a fringe pattern appearing in a vicinity of the first diffraction peak in the second diffraction spectrum.

8. The method according to claim 1, wherein positioning the beam blocker comprises automatically analyzing the first diffraction spectrum so as to identify an angular range of the first diffraction peak, and automatically shifting the blocker to cover the identified range.

9. The method according to claim 1, wherein the converging beam of X-rays has a focus, and wherein sensing the X-rays to generate the first diffraction spectrum comprises shifting the sample out of the focus so as to increase a separation between the first and second diffraction peaks, and wherein positioning the beam blocker comprises adjusting a position of beam blocker while the sample is out of the focus, and then shifting the sample into the focus in order to generate the second diffraction spectrum.

10. The method according to claim 9, wherein sensing the X-rays to generate the first diffraction spectrum comprises shifting the sample out of the focus and capturing at least the first diffraction spectrum in an asymmetric diffraction mode.

11. The method according to claim 1, wherein directing the converging beam comprises generating a monochromatic first beam at a first wavelength using a monochromator, wherein the first beam converges to a focus on the sample, and wherein the method comprises blocking a second beam generated by the monochromator at a second wavelength at a location adjacent to the first beam and before the focus.

12. A method for analysis, comprising:
directing a converging beam of X-rays, having a focus, toward a surface of a sample having first and second crystalline layers, with different, respective crystal characteristics;
sensing the X-rays that are diffracted from the sample while resolving the sensed X-rays as a function of angle so as to generate a diffraction spectrum comprising at least a first diffraction peak due to the first layer and a second diffraction peak due to the second layer;
shifting the sample out of the focus so as to increase a separation between the first and second diffraction peaks in the diffraction spectrum, wherein shifting the sample comprises measuring the separation as a function of a distance of the sample from the focus; and
analyzing the diffraction spectrum so as to identify a characteristic of at least the second layer.

13. The method according to claim 12, wherein the X-rays in the converging beam impinge on the sample over a range of incidence angles, and wherein sensing the X-rays comprises detecting the X-rays in an asymmetric mode, in which the X-rays are diffracted from the sample at takeoff angles that are different from the incidence angles.

14. The method according to claim 13, wherein the second layer is deposited epitaxially over the first layer, and wherein analyzing the diffraction spectrum comprises detecting a relaxation of the second layer relative to the first layer.

15. The method according to claim 13, wherein the converging beam of the X-rays impinges on a spot on the surface of the sample, and wherein the method comprises positioning a beam limiter to block a portion of the X-rays in a location adjacent to the spot so as to reduce a dimension of the spot.

16. The method according to claim 12, wherein analyzing the diffraction spectrum comprises finding a concentration of a dopant in the second layer based on a functional dependence of the separation on the distance of the sample from the focus.

17. A method for analysis, comprising:
directing a converging beam of X-rays to impinge over a range of incidence angles on a spot on a surface of a sample having an epitaxial layer formed thereon;
positioning a beam limiter to block a portion of the X-rays in a location adjacent to the spot so as to reduce a dimension of the spot, wherein the beam limiter has a hole configured for passage of the X-rays therethrough, such that the dimension of the spot is determined by a size of the hole;
sensing the X-rays that are diffracted from the spot in an asymmetric mode, in which the X-rays are diffracted from the sample at takeoff angles that are different from the incidence angles, while resolving the sensed X-rays as a function of takeoff angle so as to generate a diffraction spectrum; and
analyzing the diffraction spectrum in order to identify a characteristic of the epitaxial layer.

18. The method according to claim 17, wherein the beam limiter comprises a knife edge, which is positioned parallel to the surface over the spot.

19. The method according to claim 17, wherein the incidence angles fall within a range of grazing angles.

20. The method according to claim 17, wherein the takeoff angles fall within a range of grazing angles.

21. A method for analysis, comprising:
directing a converging beam of X-rays toward a surface of a sample having an epitaxial layer formed thereon, wherein the sample comprises a crystalline substrate, which diffracts the X-rays so as to generate a substrate diffraction peak;
sensing the X-rays that are diffracted from the sample while resolving the sensed X-rays as a function of angle so as to generate a diffraction spectrum comprising a diffraction peak and fringes due to the epitaxial layer,
wherein directing the converging beam comprises positioning a beam blocker in the converging beam so as to block a range of angles in the converging beam that corresponds to the substrate diffraction peak while enhancing detection of the fringes at angles adjacent to the range that is blocked; and
analyzing a characteristic of the fringes in order to measure a relaxation of the epitaxial layer.

22. The method according to claim 21, wherein analyzing the characteristic comprises assessing an amplitude of the fringes, wherein a reduction in the amplitude is indicative of an increase in the relaxation.

23. A method for analysis, comprising:
directing a converging beam of X-rays toward a focus on a surface of a crystalline sample;
scanning a slit across the converging beam so as to cause the X-rays in the beam to be incident on the sample at a sequence of angles of incidence over an angular range of the beam;
at each of the angles of incidence, sensing the X-rays that are diffracted from the sample while resolving the sensed X-rays as a function of takeoff angle so as to generate diffraction data with respect to each of the angles of incidence; and
combining the diffraction data with respect to the angles of incidence over the angular range so as to generate a reciprocal space map of diffraction from the sample.

24. Apparatus for analysis, comprising:
an X-ray source, which is configured to direct a converging beam of X-rays toward a surface of a sample having first and second crystalline layers, with different, respective crystal characteristics, whereby the X-rays are diffracted from the sample so as to generate a diffraction spectrum comprising at least a first diffraction peak due to the first layer and a second diffraction peak due to the second layer;
a detector assembly, which is configured to sense the X-rays that are diffracted from the sample while resolving the sensed X-rays as a function of angle;
a beam blocker, which is configured to be positioned in the converging beam so as to block a range of angles in the converging beam that corresponds to the first diffraction peak; and a processor, which is coupled to receive and process an output of the detector assembly, while the range of the angles containing the first diffraction peak is blocked, so as to identify a characteristic of at least the second layer based on the diffraction spectrum, wherein the beam blocker is configured to be further positioned so as not to block the range of angles in the converging beam that corresponds to the first diffraction peak, and wherein the processor is configured to analyze the diffraction spectrum while the range of angles in the converging beam that corresponds to the first diffraction peak is not blocked so as to identify an angular range corresponding to the first diffraction peak, and to cause a shift in the position of the blocker so as to cover the identified range.

25. The apparatus according to claim 24, wherein the detector assembly comprises a detector array having elements configured to capture and resolve the X-rays over a range of elevation angles simultaneously.

26. The apparatus according to claim 25, wherein the range is at least 2 degrees.

27. The apparatus according to claim 24, wherein the second layer is deposited epitaxially over the first layer.

28. The apparatus according to claim 27, wherein the first layer comprises a semiconductor substrate, and the second layer comprises a doped semiconductor.

29. The apparatus according to claim 28, wherein the semiconductor substrate comprises a silicon wafer, and the second layer comprises a SiGe epitaxial layer.

30. The apparatus according to claim 24, wherein the processor is configured to analyze a fringe pattern appearing in a vicinity of the first diffraction peak in the diffraction spectrum.

31. The apparatus according to claim 24, wherein the converging beam of X-rays has a focus, and wherein the apparatus comprises a motion device, which is configured to shift the sample out of the focus so as to increase a separation between the first and second diffraction peaks, and wherein the beam blocker is configured to be adjusted into a position in which the first diffraction peak is blocked while the sample is out of the focus, and to maintain the position when the sample is shifted into the focus in order to generate the diffraction spectrum.

32. The apparatus according to claim 31, wherein the X-ray source and the detector assembly are positionable so as to generate the diffraction spectrum in an asymmetric diffraction mode, and wherein the separation between the first and second diffraction peaks increases as the sample is shifted out of the focus in the asymmetric diffraction mode.

33. The apparatus according to claim 24, wherein the X-ray source comprises a monochromator, and wherein the converging beam comprises a monochromatic first beam at a first wavelength generated by the monochromator, wherein the first beam converges to a focus on the sample, and wherein the apparatus comprises a further beam blocker, which is configured to block a second beam generated by the monochromator at a second wavelength at a location adjacent to the first beam and before the focus.

34. Apparatus for analysis, comprising:
an X-ray source, which is configured to direct a converging beam of X-rays toward a surface of a sample having first and second crystalline layers, with different, respective crystal characteristics, whereby the X-rays are diffracted from the sample so as to generate a diffraction spectrum comprising at least a first diffraction peak due to the first layer and a second diffraction peak due to the second layer;
a detector assembly, which is configured to sense the X-rays that are diffracted from the sample while resolving the sensed X-rays as a function of angle;
a motion device, which is configured to shift the sample out of the focus so as to increase a separation between the first and second diffraction peaks in the diffraction spectrum; and
a processor, which is coupled to receive and process an output of the detector assembly, while the sample is shifted out of the focus, wherein the processor is configured to measure the separation between the first and second diffraction peaks as a function of a distance of the sample from the focus, so as to identify a characteristic of at least the second layer based on the diffraction spectrum.

35. The apparatus according to claim 34, wherein the X-rays in the converging beam impinge on the sample over a range of incidence angles, and wherein the X-ray source and the detector assembly are positionable so as generate the diffraction spectrum in an asymmetric diffraction mode, in which the X-rays are diffracted from the sample at takeoff angles that are different from the incidence angles, and wherein the processor is configured to receive and analyze the diffraction spectrum while the sample is shifted out of the focus in the asymmetric diffraction mode.

36. The apparatus according to claim 35, wherein the second layer is deposited epitaxially over the first layer, and wherein the processor is configured to measure a relaxation of the second layer relative to the first layer based on the diffraction spectrum.

37. The apparatus according to claim 35, wherein the converging beam of the X-rays impinges on a spot on the surface of the sample, and wherein the apparatus comprises a beam limiter, which is positionable so as to block a portion of the X-rays in a location adjacent to the spot so as to reduce a dimension of the spot.

38. The apparatus according to claim 34, wherein the processor is configured to find a concentration of a dopant in the second layer based on a functional dependence of the separation on the distance of the sample from the focus.

39. Apparatus for analysis, comprising:
an X-ray source, which is configured to direct a converging beam of X-rays to impinge over a range of incidence angles on a spot on a surface of a sample having an epitaxial layer formed thereon, whereby the X-rays are diffracted from the sample so as to generate a diffraction spectrum;
a beam limiter, which is configured to block a portion of the X-rays in a location adjacent to the spot so as to reduce a dimension of the spot, wherein the beam limiter has a hole configured for passage of the X-rays therethrough, such that the dimension of the spot is determined by a size of the hole;
a detector assembly, which is configured to sense the X-rays that are diffracted from the spot in an asymmetric mode, in which the X-rays are diffracted from the sample at takeoff angles that are different from the incidence angles, while resolving the sensed X-rays as a function of takeoff angle; and
a processor, which is coupled to receive and process an output of the detector assembly so as to identify a characteristic of the epitaxial layer based on the diffraction spectrum.

40. The apparatus according to claim 39, wherein the beam limiter comprises a knife edge, which is positioned parallel to the surface over the spot.

41. The apparatus according to claim 39, wherein the incidence angles fall within a range of grazing angles.

42. The apparatus according to claim 39, wherein the takeoff angles fall within a range of grazing angles.

* * * * *